(12) United States Patent
Nolte et al.

(10) Patent No.: US 7,405,831 B2
(45) Date of Patent: *Jul. 29, 2008

(54) LASER SCANNING INTERFEROMETRIC SURFACE METROLOGY

(75) Inventors: David Nolte, Lafayette, IN (US); Manoj Varma, West Lafayette, IN (US); Fred E. Regnier, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/345,564

(22) Filed: Feb. 1, 2006

(65) Prior Publication Data

US 2006/0256350 A1    Nov. 16, 2006

Related U.S. Application Data

(60) Provisional application No. 60/649,071, filed on Feb. 1, 2005, provisional application No. 60/649,043, filed on Feb. 1, 2005, provisional application No. 60/648,724, filed on Feb. 1, 2005, provisional application No. 60/649,070, filed on Feb. 1, 2005, provisional application No. 60/755,177, filed on Dec. 30, 2005.

(51) Int. Cl.
*G01B 11/02* (2006.01)
(52) U.S. Cl. .................................... 356/511
(58) Field of Classification Search ............. 356/484, 356/485, 489, 511, 512, 516
See application file for complete search history.

(56) References Cited

U.S. PATENT DOCUMENTS 3,796,495 A * 3/1974 Laub ..................... 356/489

4,537,861 A    8/1985   Elings et al.

(Continued)

FOREIGN PATENT DOCUMENTS

EP    1189062 A1    3/2002

(Continued)

OTHER PUBLICATIONS

Xia, Y, et al. Non Photolithographic Methods and Fabrication of Elastomeric Stamps for Use in Microcontact Printing, Langmuir, 1996, Vo. 12, pp. 4033-4038.

(Continued)

*Primary Examiner*—Michael A Lyons
(74) *Attorney, Agent, or Firm*—Bose McKinney & Evans LLP

(57) ABSTRACT

An apparatus for assessing topology of a surface of a target including an optical source for generating a probe laser beam. The apparatus also includes a means for scanning the probe laser beam across at least a portion of the surface of the target and a beamsplitter for redirecting a return signal toward the means for detecting the return signal in a substantially quadrature condition. A quadrature interferometric method for determining the presence or absence of a target analyte in a sample comprising a laser probe beam having a wavelength $\lambda$ and a waist $w_o$ to probe at least a portion of a substrate having a reflecting surface that includes at least a first region having a layer of recognition molecules specific to the target analyte and a second region that does not include a layer of recognition molecules specific to the target analyte.

28 Claims, 10 Drawing Sheets

U.S. PATENT DOCUMENTS

| | | | |
|---|---|---|---|
| 4,741,620 A * | 5/1988 | Wickramasinghe | 356/489 |
| 4,876,208 A | 10/1989 | Gustafson et al. | |
| 4,975,237 A | 12/1990 | Brown | |
| 5,122,284 A | 6/1992 | Braynin et al. | |
| 5,155,549 A | 10/1992 | Dhadwal | |
| 5,413,939 A | 5/1995 | Gustafson et al. | |
| 5,478,527 A | 12/1995 | Gustafson et al. | |
| 5,494,829 A * | 2/1996 | Sandstrom et al. | 436/518 |
| 5,545,531 A | 8/1996 | Rava et al. | |
| 5,631,171 A | 5/1997 | Sandstrom et al. | |
| 5,653,939 A | 8/1997 | Hollis et al. | |
| 5,717,778 A | 2/1998 | Chu et al. | |
| 5,736,257 A | 4/1998 | Conrad et al. | |
| 5,781,649 A | 7/1998 | Brezoczky | |
| 5,786,226 A | 7/1998 | Bocker et al. | |
| 5,837,475 A | 11/1998 | Dorsel et al. | |
| 5,843,767 A | 12/1998 | Beattie | |
| 5,844,871 A | 12/1998 | Maezawa | |
| 5,874,219 A | 2/1999 | Rava et al. | |
| 5,875,029 A | 2/1999 | Jann et al. | |
| 5,892,577 A | 4/1999 | Gordon | |
| 5,900,935 A | 5/1999 | Klein et al. | |
| 5,922,617 A | 7/1999 | Wang et al. | |
| 5,935,785 A | 8/1999 | Reber et al. | |
| 5,945,344 A | 8/1999 | Hayes et al. | |
| 5,955,377 A | 9/1999 | Maul et al. | |
| 5,968,728 A | 10/1999 | Perttunen et al. | |
| 6,008,892 A | 12/1999 | Kain et al. | |
| 6,030,581 A | 2/2000 | Virtanen | |
| 6,048,692 A | 4/2000 | Maracas et al. | |
| 6,060,237 A | 5/2000 | Nygren et al. | |
| 6,071,748 A | 6/2000 | Modlin et al. | |
| 6,099,803 A | 8/2000 | Ackley | |
| 6,110,748 A | 8/2000 | Reber et al. | |
| 6,121,048 A | 9/2000 | Zaffaroni et al. | |
| 6,140,044 A | 10/2000 | Besemer et al. | |
| 6,143,247 A | 11/2000 | Sheppard, Jr. et al. | |
| 6,177,990 B1 | 1/2001 | Kain et al. | |
| 6,221,579 B1 | 4/2001 | Everhart et al. | |
| 6,238,869 B1 | 5/2001 | Kris et al. | |
| 6,248,539 B1 | 6/2001 | Ghadiri et al. | |
| 6,249,593 B1 | 6/2001 | Chu et al. | |
| 6,256,088 B1 | 7/2001 | Gordon | |
| 6,271,924 B1 * | 8/2001 | Ngoi et al. | 356/489 |
| 6,287,783 B1 | 9/2001 | Maynard et al. | |
| 6,287,850 B1 | 9/2001 | Besemer et al. | |
| 6,312,961 B1 | 11/2001 | Voirin et al. | |
| 6,319,468 B1 | 11/2001 | Sheppard, Jr. et al. | |
| 6,319,469 B1 | 11/2001 | Mian et al. | |
| 6,320,665 B1 | 11/2001 | Ngoi et al. | |
| 6,327,031 B1 | 12/2001 | Gordon | |
| 6,339,473 B1 | 1/2002 | Gordon | |
| 6,342,349 B1 | 1/2002 | Virtanen | |
| 6,342,395 B1 | 1/2002 | Hammock et al. | |
| 6,345,115 B1 | 2/2002 | Ramm et al. | |
| 6,350,413 B1 | 2/2002 | Reichert et al. | |
| 6,355,429 B1 | 3/2002 | Nygren et al. | |
| 6,368,795 B1 | 4/2002 | Hefti | |
| 6,376,258 B2 | 4/2002 | Hefti | |
| 6,381,025 B1 | 4/2002 | Bornhop et al. | |
| 6,387,331 B1 | 5/2002 | Hunter | |
| 6,395,558 B1 | 5/2002 | Duveneck et al. | |
| 6,395,562 B1 | 5/2002 | Hammock et al. | |
| 6,399,365 B2 | 6/2002 | Besemer et al. | |
| 6,403,957 B1 | 6/2002 | Fodor et al. | |
| 6,416,642 B1 | 7/2002 | Alajoki et al. | |
| 6,469,787 B1 | 10/2002 | Meyer et al. | |
| 6,476,907 B1 | 11/2002 | Gordon | |
| 6,483,585 B1 | 11/2002 | Yang | |
| 6,496,309 B1 | 12/2002 | Bliton et al. | |
| 6,504,618 B2 | 1/2003 | Morath et al. | |
| 6,518,056 B2 | 2/2003 | Schembri et al. | |
| 6,551,817 B2 | 4/2003 | Besemer et al. | |
| 6,566,069 B2 | 5/2003 | Virtanen | |
| 6,584,217 B1 | 6/2003 | Lawless et al. | |
| 6,596,483 B1 | 7/2003 | Choong et al. | |
| 6,602,702 B1 | 8/2003 | McDevitt et al. | |
| 6,623,696 B1 | 9/2003 | Kim et al. | |
| 6,624,896 B1 | 9/2003 | Neal et al. | |
| 6,649,403 B1 | 11/2003 | McDevitt et al. | |
| 6,653,152 B2 | 11/2003 | Challener | |
| 6,685,885 B2 | 2/2004 | Nolte et al. | |
| 6,687,008 B1 | 2/2004 | Peale et al. | |
| 6,709,869 B2 | 3/2004 | Mian et al. | |
| 6,720,177 B2 | 4/2004 | Ghadiri et al. | |
| 6,733,977 B2 | 5/2004 | Besemer et al. | |
| 6,737,238 B2 | 5/2004 | Suzuki et al. | |
| 6,743,633 B1 | 6/2004 | Hunter | |
| 6,760,298 B2 | 7/2004 | Worthington et al. | |
| 6,770,447 B2 | 8/2004 | Maynard et al. | |
| 6,787,110 B2 | 9/2004 | Tiefenthaler | |
| 6,791,677 B2 | 9/2004 | Kawai et al. | |
| 6,803,999 B1 | 10/2004 | Gordon | |
| 6,806,963 B1 | 10/2004 | Walti et al. | |
| 6,819,432 B2 | 11/2004 | Pepper et al. | |
| 6,836,338 B2 | 12/2004 | Opsal et al. | |
| 6,844,965 B1 | 1/2005 | Engelhardt | |
| 6,847,452 B2 | 1/2005 | Hill | |
| 6,878,555 B2 | 4/2005 | Anderson et al. | |
| 6,897,965 B2 | 5/2005 | Ghadiri et al. | |
| 6,917,421 B1 | 7/2005 | Wihl et al. | |
| 6,917,432 B2 | 7/2005 | Hill et al. | |
| 6,937,323 B2 | 8/2005 | Worthington et al. | |
| 6,955,878 B2 | 10/2005 | Kambara et al. | |
| 6,958,131 B2 | 10/2005 | Tiefenthaler | |
| 6,980,299 B1 | 12/2005 | de Boer | |
| 6,987,569 B2 | 1/2006 | Hill | |
| 6,992,769 B2 | 1/2006 | Gordon | |
| 6,995,845 B2 | 2/2006 | Worthington | |
| 7,008,794 B2 | 3/2006 | Goh et al. | |
| 7,012,249 B2 | 3/2006 | Krutchinsky et al. | |
| 7,014,815 B1 | 3/2006 | Worthington et al. | |
| 7,026,131 B2 | 4/2006 | Hurt et al. | |
| 7,027,163 B2 | 4/2006 | Angeley | |
| 7,031,508 B2 | 4/2006 | Lawless et al. | |
| 7,033,747 B2 | 4/2006 | Gordon | |
| 7,061,594 B2 | 6/2006 | Worthington et al. | |
| 7,070,987 B2 | 7/2006 | Cunningham et al. | |
| 7,077,996 B2 | 7/2006 | Randall et al. | |
| 7,083,920 B2 | 8/2006 | Werner et al. | |
| 7,087,203 B2 | 8/2006 | Gordon et al. | |
| 7,088,650 B1 | 8/2006 | Worthington et al. | |
| 7,091,034 B2 | 8/2006 | Virtanen | |
| 7,091,049 B2 | 8/2006 | Boga et al. | |
| 7,094,609 B2 | 8/2006 | Demers | |
| 7,098,041 B2 | 8/2006 | Kaylor et al. | |
| 7,102,752 B2 | 9/2006 | Kaylor et al. | |
| 7,106,513 B2 | 9/2006 | Moon et al. | |
| 7,110,094 B2 | 9/2006 | Gordon | |
| 7,110,345 B2 | 9/2006 | Worthington et al. | |
| 7,118,855 B2 | 10/2006 | Cohen et al. | |
| 7,141,378 B2 | 11/2006 | Miller et al. | |
| 7,141,416 B2 | 11/2006 | Krutzik | |
| 7,145,645 B2 | 12/2006 | Blumenfeld et al. | |
| 7,148,970 B2 | 12/2006 | de Boer | |
| 7,200,088 B2 | 4/2007 | Worthington et al. | |
| 7,221,632 B2 | 5/2007 | Worthington | |
| 2001/0055812 A1 | 12/2001 | Mian et al. | |
| 2002/0001546 A1 | 1/2002 | Hunter et al. | |
| 2002/0008871 A1 | 1/2002 | Poustka et al. | |
| 2002/0045276 A1 | 4/2002 | Yguerabide et al. | |
| 2002/0051973 A1 | 5/2002 | Delenstarr et al. | |
| 2002/0085202 A1 | 7/2002 | Gordon | |
| 2002/0106661 A1 | 8/2002 | Virtanen | |

| | | | |
|---|---|---|---|
| 2002/0135754 | A1 | 9/2002 | Gordon |
| 2002/0151043 | A1 | 10/2002 | Gordon |
| 2003/0054376 | A1 | 3/2003 | Mullis et al. |
| 2003/0133640 | A1 | 7/2003 | Tiefenthaler |
| 2003/0134330 | A1 | 7/2003 | Ravkin et al. |
| 2004/0002085 | A1 | 1/2004 | Schembri et al. |
| 2004/0106130 | A1 | 6/2004 | Besemer et al. |
| 2004/0132172 | A1 | 7/2004 | Cunningham et al. |
| 2004/0150829 | A1 | 8/2004 | Koch et al. |
| 2004/0166525 | A1 | 8/2004 | Besemer et al. |
| 2004/0166593 | A1 | 8/2004 | Nolte et al. |
| 2004/0229254 | A1 | 11/2004 | Clair |
| 2004/0247486 | A1 | 12/2004 | Tiefenthaler |
| 2004/0258927 | A1 | 12/2004 | Conzone et al. |
| 2005/0002827 | A1 | 1/2005 | McIntyre et al. |
| 2005/0003459 | A1 | 1/2005 | Krutzik |
| 2005/0019901 | A1 | 1/2005 | Matveeva et al. |
| 2005/0042628 | A1 | 2/2005 | Rava et al. |
| 2005/0084895 | A1 | 4/2005 | Besemer et al. |
| 2005/0106746 | A1 | 5/2005 | Shinn et al. |
| 2005/0123907 | A1 | 6/2005 | Rava et al. |
| 2005/0158819 | A1 | 7/2005 | Besemer et al. |
| 2005/0176058 | A1 | 8/2005 | Zaffaroni et al. |
| 2005/0191630 | A1 | 9/2005 | Besemer et al. |
| 2005/0214950 | A1 | 9/2005 | Roeder et al. |
| 2005/0226769 | A1 | 10/2005 | Shiga |
| 2005/0259260 | A1 | 11/2005 | Wakita |
| 2006/0040380 | A1 | 2/2006 | Besemer et al. |
| 2006/0078935 | A1 | 4/2006 | Werner et al. |
| 2006/0204399 | A1 | 9/2006 | Freeman et al. |
| 2006/0210449 | A1 | 9/2006 | Zoval et al. |
| 2006/0223172 | A1 | 10/2006 | Bedingham et al. |
| 2006/0234267 | A1 | 10/2006 | Besemer et al. |
| 2006/0256676 | A1* | 11/2006 | Nolte et al. ............... 369/47.1 |
| 2006/0257939 | A1 | 11/2006 | Demers |
| 2006/0269450 | A1 | 11/2006 | Kim et al. |
| 2006/0270064 | A1 | 11/2006 | Gordon et al. |
| 2007/0003436 | A1* | 1/2007 | Nolte et al. ................. 422/64 |
| 2007/0003979 | A1 | 1/2007 | Worthington |
| 2007/0070848 | A1 | 3/2007 | Worthington et al. |
| 2007/0077599 | A1 | 4/2007 | Krutzik |
| 2007/0077605 | A1 | 4/2007 | Hurt et al. |

FOREIGN PATENT DOCUMENTS

| | | |
|---|---|---|
| WO | WO 9104489 | 4/1991 |
| WO | WO 9104491 | 4/1991 |
| WO | WO 9113353 | 9/1991 |
| WO | WO 9837238 | 8/1998 |

OTHER PUBLICATIONS

Hu, J., et al. Using Soft Lithography to Fabricate GaAs/AlGaAs Hetreostructure Field Effect Transistors, Appl. Phys.Lett.,1997 vol. 71, pp. 2020-2002.

Grzybowski, B.A., et al., Generation of Micrometer-Sized Patterns for Microanalytical Applications Using a Laser Direct-Write Method and Microcontact Printing, Anal. Chem., 1998, Vol. 70, p. 4645-4652.

Martin, B.D., et al., Direct Protein Microarray Fabrication Using a Hydrogel Stamper, Langmuir, 1998, vol. 14, pp. 3971-3975.

Pompe, T., et al., Submicron Contact Printing On Silicon Using Stamp Pads, Langmuir, 1999, vol. 15, pp. 2398-2401.

Bietsch, A. and B. Michel, Conformal Contact And Pattern Stability of Stamps Used For Soft Lithography, J. Appl. Phys., 2000, vol. 88, pp. 4310-4318.

Geissler, M., et al., Mictrocontact Printing Chemical Patterns With Flat Stamps, J. Am. Chem. Soc., 2000, vol. 122, pp. 6303-6304.

Sanders, G.H.W. and A. Manz, Chip-based Microsystems For Genomic And Proteomic Analysis, Trends in Anal. Chem., 2000, vol. 19(6), pp. 3465-378.

Wang, J., Survey and Summary From DNA Biosensors To Gene Chips, Nucl. Acids Res., 2000 vol. 28(16), pp. 3011-3016.

Hagman, M., Doging Immunology On A Chip, Science, 2000, vol. 290, pp. 82-83.

Marx, J., DNA Arrays Reveal Cancer In Its Many Forms, Science, 2000, vol. 289, pp. 1670-1672.

Effenhauser, C.S., et al., Integrated Capillary Electrophoresis On Flexible Silicon Microdevices: Analysis of DNA Restriction Fragments And Detection Of Single DNA Molecules On Microchips. Anal. Chem., 1997, vol. 69, pp. 3451-3457.

He, B. and F.E.. Regnier, Fabrication of Nanocolumns for Liquid Chromatography, Anal. Chem., 1998, vol. 70, p. 3790-3797.

Kricka, L.J., Miniaturization of Analytical Systems. Clin. Chem., 1998, vol. 44(9), pp. 2008-2014.

Regnier, F.E., et al., Chromatography and Electrophoresis On Chips: Critical Elements Offuture Integrated, Microfluidic Analytical Systems For Life Science. Tibtdch, 1999, vol. 17, pp. 101-106.

Ekins, R.,F. Chu, and E. Biggart, Develpoment of Microspot Multi-Analyte Ratiometric Immunoassay Using Dual Flourescent-Labelled Antibodies. Anal. Chim. Acta, 1989, vol. 227, pp. 73-96.

Gao, H., et al., Immunosensing With Photo-Immobilized Immunoreagents On Planar Optical Wave Guides. Biosensors and Bioelecctronics, 1995, vol. 10, pp. 317-328.

Maisenholder, B., et al., A GaAs/AlGaAs-based Refractometer Platform For Integrated Optical Sensing Applications. Sensors and Actuators B, 1997, vol. 38-39, pp. 324-329.

Kunz, R.E., Miniature Integrated Optical Modules For Chemical and Biochemical Sensing. Sensors and Actuators B, 1997, vol. 38-39, pp. 13-28.

DuBendorfer, J. and R.E. Kunz, Reference Pads For Miniaure Integrated Optical Sensors. Sensors and Actuatores B, 1997 vol. 38-39, pp. 1-7.

Hecht, E., Optics, 1987: Addison-Wesley publishing Co., Inc.

Scruby, C.B. and L.E. Drain, Laser Ultrasonics: Techniques and Applications. 1990, Bristol: Adam Hilger.

Nolte, D.D. , et al., Adaptive Beam Combining and Interferometry Using Photorefractive Quantum Wells, J. Opt. Soc. Am. B, vol. 19, No. 2, Feb. 2001, pp. 195-205.

St. John et al., "Diffraction-Based Cell Detection Using a Microcontact Printed Antibody Grating", Analytical Chemistry, 1998, vol. 70, No. 6, pp. 1108-1111.

Morhard, F., et al., Immobilization Of Antibodies in Micropatterns For Cell Detection By Optical Diffraction. Sensors and Actuators B, 2000, vol. 70, pp. 232-242.

I. Rossomakhin and. Stepanov, Linear Adaptive Interferometers Via Diffusion Recording In Cubic Photorefractive Crystals, Opt. Commun. 86, 199-204 (1991).

Ing R.K and Monchalin, L.P. , Broadband Optical Detection of Ultrasound By Two-Wave Mixing In A Photorefractive Crystal, Appl. Phys. Lett. 59, 3233-5 (1991).

Delaye, P. et al., Detection of Ultraonic Motion of a Scattering Surface by Two-Wave Mixing In a Photorefractive GaAs Crystal, Appl. Phys. Litt. 65, 932-4 (1994).

Pouet, B.F. Ing, R.K., Krishnaswanry, S, and Royer, D, Heterodyne Interferometer With Two-Wave Mixing In Photorefractive Crystals For Ultrasound Detection On Rough Surface, Appl. Phys. Lett. 69, 3782 (1996).

Montmorillon, L.A. Biaggio, I Delaye, P. Launay, J.-C., and Roosen, A, Eye Safe Large Field of View Homodyne Detection Using a Photorefractive CdTe: V Crystal, Opt. Commun. 29, 293 (1996).

P. Delaye, A. Blouin, D. Drolet, L.-A. Montmorrillong. Roosen,and J.-P Monchalin, Detection of Ultrasonice Motion of a Scattering Surface by Photorefractive InP:Fe Under An Applied dc Field, J. Opt. Soc. Am. B14, 1723-34 (1997).

I, Lahiri, L.J. Pyrak-Nolte, D.D. Nolte, M.R. Melloch, R.A. Kruger, G.D. Backer, and M. B. Klein, Laser-Based Ultrasound Detection Using Photorefractive Uantum Wells, Appl. Phys. Lett. 73, 1041-43 (1998).

S. Balassubramanian, L.Lahiri, Y. Ding, M.R. Melloch, and D.D. Nolte, Two-Wave Mixing Dynamics And Nonlinear Hot-Electorn Transport In Transverse-Geometry Photorefractive Quantum Wells Studies By Moving Grantings, Appl. Phys. B. 68, 863-9 (1990).

E. Delmarche, A. Bernard, II. Schmid, B. Michel, and H. Biebuyck, Patterned Delivery of Immonglobulines to Surface Using Microfluidic Networks, Science 276, 779-781(1997).

E. Delamarche, A. Bernard, H. Schmid, A. Bietsch, 13 Michel, and H. Blebuyck, Microfluidic Networks For Chemical Patterning of Substrates: Design and Application to Bioassays, Journal of the American Chemical Society 120, 500-508 (1998).

Kapur, Ravi et al. Streamlining the Drug Discovery Process by Integrating Miniaturization High Throughput Screening, High Content Screening, and Automation on the CellChip TM System, Biomedical Microdevices, vol. 1, No. 2, 1999, pp. 99-109.

Ekins R. et al. Multianalyte Microspot Immunoassay, The Microanalytical Compact Disk Of The Future: Clin. Chem., 1991, Vo. 37(11), p. 1955-1967.

Jenison, R., Yan, S. Haeberli, A. Polisky, B., 2001. Interference-Based Detection of Nucleic Acid Targets On Optically Coated Silicon. Nat. Biotechnol. 19, pp. 62-65.

Fattinger, C., Koller, H., Schlatter, D., Wehrli, P., 1993, The Difference Interferometer-A High Sensitive Optical Probel For Quantification Of Molecular-Surface Concentration; Biosens, Bioelectron 8, pp. 99-107.

Jenison, Robert et al., Silicon-based Biosensors for Rapid Detection of Protein or Nucleic Acid Targets, Clinical Chemistry, 47:10, 2001 pp. 1894-1990.

Varma., M.M., et al.; High Speed Lable Free Detection By Spinning-Disk Micro-Interferomerty; Biosensors & Bioelectronics, vol. 19, pp. 1371-1376, 2004.

Varma, M.M, et al.; Spinning-Disk Self-Referencing Interferrometry of Antigen-Antibody Recognition; Optics Lettters, vol. 29, pp. 950-952, 2004.

Morhard et al.; Immobilization of Antibodies in Micropatterns for Cell Detection by Optical Diffraction, Sensors and Actuators B., 2000, vol. 70, pp. 232-242.

Nolte, D.D.; Semi-insulating Semiconductor Heterostructures: Optoelectronic Properties And Applications, J.Appl.Phys. vol. 85, pp. 6269, 1999.

Brecht, A. and G. Gauglitz; Recent Developements in Optical Transducers for Chemical of Biochemical Applications. Sensors and Actuators B, 1997 vol. 38-39, pp. 1-7.

Varma, M.M. et al.; High-Speed Label-Free Multi-Analyte Detection Through Micro-Interferometry; Proc. of SPIE, vol. 496, pp. 58-65, 2003.

Ekins, R., Ligand, Assays; From Electrophoresis to Miniaturized Microaarays, Clin. Chem, 1998, vol. 44(9), pp. 2015-2030.

Somekh, Michael et al.; Scanning Heterodyne Confocal Differential Phase And Intensity Microscope, Applied Optics, vol. 34, No. 22, pp. 4857-4868; 1995.

Suddendorf, Manfred, et al.; Single-Probe-Beam Differential Amplitude And Phase-Scanning Interferometer; vol. 36, No. 25, pp. 6202-6210, 1997.

See, C.W. et al.; Scanning Differential Optical Profilometer For Simultaneous Measurement Of Amplitude and Phase Variation, Appl. Phys. Lett, vol. 53, No. 1, pp. 10-12, 1988.

Abe, Takao, et al. Microroughness Measurements on Polished Silicon Wafers, Jpn. J. Appl. Phys., vol. 31, pp. 721-728, 1992.

Nolte, D.D. et al.; Spinning-Disk Interferometry The BioCD; Optics & Photonics News, pp. 48-53, 2004.

Ding, Y., et al.; Femtosecnd Pulse By Dynamic Holograms In Photorefractive Multiple Quantum Wells; Optical Society of America, pp. 718-720; 1997.

Ding, Y., et al., Adaptive All-Order Dispersion Compensation Of Ultrafast Laser Pulses Using Dynamic Spectral Holography; American Institute of Physics, pp. 3255-3257; 1999.

Jones, R. et al.; Adaptive Femtosecond Optical Pulse Combining; American Institute of Physics, pp. 3692-3694; 2000.

Lahiri, I et al.; Photorefractice p-i-n Diode AQuantum Well Spatial Light Modulators; American Institute of Physics, pp. 1408-1738; 1995.

Notle, D.D., Self-Adaptive Optical Hologrpy In Quantum Wells, pp. 1-6, 2005.

La Clair, J. et al.; Molecular Screeing On A Compact Disc; The Royal Society of Chemistry; pp. 3244-3249; 2003.

Burkart, et al. UCSD Scientists Develope Novel Way to Screen Molecules Using Conventional CDS an Compact Disk Players; UCSD newsletter; pp. 1-4, 2003.

Kwolek, K.M. et al.; Photorefractive Asymmetric Fabry-Perot Quantum Wells: Transverse-filed Geometry; Appl. Phys. Lett, vol. 67, pp. 736-738, 1995.

Nolte, D, et al., Photofreactive Quantum Wells, 2005.

Peng, Lellel et al., Adaptive Optical biocompact Disk For Moecular Recognition, Applied Physics Letters 86, 2005.

Blouin, A., et al., Detection of Ultrasonic Motion of a Scattering Surface by Two-Wave Mixing in a Photorefractive GaAs Crystal, Appl. Phys. Lett., vol. 65, pp. 932-934 (1994).

Nolte, D.D., Self-Adaptive Optical Holography in Quantum Wells, Pro. Of SPIE, vol. 37:29, pp. 237-243 (1999).

Nolte, D., et al. Photorefractive Quantum Wells (Nov. 2004).

* cited by examiner

LASER SCANNING INTERFEROMETRIC SURFACE METROLOGY

RELATED APPLICATIONS

This application claims priority to U.S. Provisional Patent Application No. 60/649,071, filed Feb. 1, 2005, entitled "Laser Scanning Inteferometric Assays".

This application also claims priority to four additional U.S. provisional applications: (1) U.S. Provisional Application No. 60/649,043, filed Feb. 1, 2005, entitled "Multiplexed Laser-Scanning Interferometric Biochips and Biodisks" [and also U.S. application Ser. No. 11/345,477 being filed on the same day as the present application that claims priority to this provisional application and entitled "Multiplexed Biological Analyzer Planar Array Apparatus and Methods"]; (2) U.S. Provisional Application No. 60/648,724 filed Feb. 1, 2005, entitled "Method for Conducting Carrier-Wave Side-Band Optical Assays for Molecular Recognition" [and also U.S. patent application Ser. No. 11/345,566 being filed on the same day as the present application that claims priority to this provisional application and entitled "Differentially Encoded Biological Analyzer Planar Array Apparatus and Methods"]; and (3) U.S. Provisional Patent Application No. 60/649,070, filed Feb. 1, 2005, entitled "Phase-Contrast Quadrature For Spinning Disk Interferometry And Immunological Assay"; and (4) U.S. Provisional Patent Application No. 60/755,177, filed Dec. 30, 2005, entitled "Phase-Contrast BioCD: High-Speed Immunoassays at Sub-Picogram Detection Levels" [U.S. provisional applications (3) and (4) resulting in U.S. patent application Ser. No. 11/345,462 being filed on the same day as the present application and entitled "Method and Apparatus for Phase Contrast Quadrature Interferometric Detection of an Immunoassay"]. All of the aforementioned utility patent applications are incorporated herein by reference.

This application is also related to pending U.S. Application Ser. No. 10/726,772 filed Dec. 3, 2003 [published as US 2004/0166593 on Aug. 26, 2004] as well as its parent application that resulted in U.S. Pat. No. 6,685,885.

FIELD OF THE INVENTION

The present invention generally relates to a device for detecting surface height changes, and more particularly to a laser scanning system for detecting the presence of surface height differences caused by surface topology and/or structure or biological pathogens and/or analyte molecules bound to target receptors by sensing changes in the optical characteristics of a probe beam reflected from the surface caused by height discontinuities or by the pathogens and/or analytes.

BACKGROUND OF THE INVENTION

In the field of material processing, it is desirable to be able from a stand-off distance to detect surface heights or densities using a laser probe. In the more specific case of chemical, biological, medical, and diagnostic applications, it is desirable to detect the presence of specific molecular structures in a sample. Many molecular structures such as cells, viruses, bacteria, toxins, peptides, DNA fragments, and antibodies are recognized by particular receptors. Biochemical technologies including gene chips, immunological chips, and DNA arrays for detecting gene expression patterns in cancer cells, exploit the interaction between these molecular structures and the receptors. [For examples see the descriptions in the following articles: Sanders, G. H. W. and A. Manz, *Chip-based micro-systems for genomic and proteomic analysis*. Trends in Anal. Chem., 2000, Vol. 19(6), p. 364-378. Wang, J., *From DNA biosensors to gene chips*. Nucl. Acids Res., 2000, Vol. 28(16), p. 3011-3016; Hagman, M., *Doing immunology on a chip*. Science, 2000, Vol. 290, p. 82-83; Marx, J., *DNA Arrays reveal cancer in its manyforms*. Science, 2000, Vol. 289, p. 1670-1672]. These technologies generally employ a stationary chip prepared to include the desired receptors (those which interact with the target analyte or molecular structure under test). Since the receptor areas can be quite small, chips may be produced which test for a plurality of analytes. Ideally, many thousand binding receptors are provided to provide a complete assay. When the receptors are exposed to a biological sample, only a few may bind a specific protein or pathogen. Ideally, these receptor sites are identified in as short a time as possible.

As a separate example, both biological chips and electronic chips (including, but not limited to, semiconductor wafers) contain complex surface structures that are fabricated as part of the function of the chip. These surface features are becoming steadily smaller, scaling now into the nanometer range. Conventional laser profilometers are not able to detect such small changes. Interferometric techniques have been successfull in this range, but require stringent vibration isolation and mechanical stability to operate.

There is a need for improved interferometric and/or techniques that may be used to measure these surface structures.

SUMMARY OF THE INVENTION

In one embodiment of the present invention there is an improved stable nanometer-scale and sub-nanometer-scale interferometric techniques that may be used to measure surface structures.

One embodiment according to the present invention includes a laser deflector unit that translates a laser probe laterally at the surface of the test object. Light reflected from the object retraces the ray path and is preferably reflected by a beam splitter into a quadrature detection system. The quadrature detection system can be comprised of several classes, including micro-diffraction [see U.S. Pat. No. 6,685,885], adaptive optic [see U.S. application Ser. No. 10/726,772 filed Dec. 3, 2003 and published as Pub. No. US 2004/0166593], and phase contrast [U.S. patent application Ser. No. 11/345,462 being filed on the same day as the present application and entitled "Method and Apparatus for Phase Contrast Quadrature Interferometric Detection of an Immunoassay"]. The quadrature detection is a transducer that converts phase modulation, imprinted on the beam by the surface topology, into direct intensity modulation that is detected by a detector, hence providing a means of detecting surface height and/or density.

In another embodiment of the present invention there is an apparatus for assessing topology of a surface of a target. The apparatus includes an optical source for generating a probe laser beam. The apparatus also includes means for scanning the probe laser beam across at least a portion of the surface of the target. The apparatus further includes a beamsplitter for redirecting a return signal toward means for detecting the return signal in a substantially quadrature condition, the return signal resulting from reflection of the probe laser beam off the surface of the target.

In one refinement of an embodiment of the invention the means for scanning includes a parallel plate.

In another refinement of an embodiment of the invention the means for scanning further includes a galvanometer for rotating the parallel plate at high speed.

In another refinement of an embodiment of the invention the means for scanning includes a deflector mirror.

In another refinement of an embodiment of the invention the means for scanning further includes a galvanometer for rotating the deflector mirror at high speed.

In another refinement of an embodiment of the invention the means for scanning is a lens that is laterally deflected.

In another refinement of an embodiment of the invention the means for scanning includes an acoutso-optic modulator.

In another refinement of an embodiment of the invention the apparatus further includes a lens with a focal length f for focusing the probe laser beam with a waist $w_o$ on the surface of the target, the lens being positioned between the means for scanning and the target.

In another refinement of an embodiment of the invention the means for detecting return signal in a substantially quadrature condition includes an adaptive optic element used in conjunction with two separate photodetectors.

In another refinement of an embodiment of the invention the adaptive optic element is a photorefractive quantum well.

In another refinement of an embodiment of the invention the means for detecting return signal in a substantially quadrature condition includes a split photodetector.

In another refinement of an embodiment of the invention the probe laser beam has a wavelength $\lambda$, and wherein the split photodetector is a detector array positioned at a pair of quadrature angles $\theta_q$, the quadrature angles being defined from a ray normal to the target by a formula: $\theta_q = \sin^{-1}(\lambda/2w_o)$.

In another refinement of an embodiment of the invention the apparatus further includes an inverting circuit and a summing circuit.

In another refinement of an embodiment of the invention the acousto-optic modulator is offset from the lens by a distance f, and wherein the lens is offset from the surface of the target by a distance f.

In another embodiment of the invention there is a quadrature interferometric method for determining the presence or absence of a target analyte in a sample. The method comprises generating a laser probe beam having a wavelength $\lambda$ and a waist $w_o$ to probe at least a portion of a substrate having a reflecting surface that has been exposed to the sample. The reflecting surface includes at least a first region having a layer of recognition molecules specific to the target analyte and a second region that does not include a layer of recognition molecules specific to the target analyte. The method also comprises scanning the first region and the second region while the substrate is maintained in a substantially fixed position. The method further comprises measuring a time dependent intensity of a reflected diffraction signal of the probe beam while scanning the probe beam across the first region and the second region.

In one refinement of an embodiment of the invention the scanning is done using an acousto-optic modulator in conjunction with a lens.

In another refinement of an embodiment of the invention the reflected diffraction signal of the laser beam is measured using a split-photodetector configuration. The method further comprising inverting a first output portion of the reflected signal corresponding to the one of the pair of quadrature angles, and summing the inverted first output with a second output of the reflected signal corresponding to the other of the pair of quadrature angles.

In another refinement of an embodiment of the invention the reflecting surface is substantially flat and the quadrature angles are defined from a ray normal to the substrate by a formula: $\theta_q = \sin^{-1}(\lambda/2w_o)$.

In another refinement of an embodiment of the invention the reflecting surface of the substrate includes a plurality of lands and a plurality of ridges, the ridges having a height h, and the quadrature angles are defined from a ray normal to the substrate by a formula: $\theta_q = \sin^{-1}[\lambda/2 - 4h)/w_o]$.

In another refinement of an embodiment of the invention the scanning is done by sweeping an angular deflection by sweeping a sound frequency in the acousto-optic modulator. The method further comprising dithering the probe laser beam, wherein the dithering is accomplished by superposing a high speed frequency on top of the slower scan frequency sweep.

In another refinement of an embodiment of the invention the method further comprises dithering the probe laser beam.

In another embodiment of the present invention there is a method for a high rate of inspection of a surface of a target using laser scanning quadrature interferometric detection. The method comprises generating a probe laser beam having a wavelength $\lambda$. The method also comprises passing the probe beam through an acousto-optic modulator for angular deflection of the probe beam and then passing the deflected beam through a lens having a focal length f to focus the probe beam to a waist $w_o$ on the surface of the target. The method further comprises measuring a time dependent intensity in a substantially quadrature condition of a reflected diffraction signal resulting from scanning the probe beam across at least a portion of the surface of the target, the scanning occurring via controlling the angular deflection caused by the acousto-optic modulator.

In one refinement of an embodiment of the invention the method further comprises dithering the probe laser beam.

In another refinement of an embodiment of the invention the quadrature condition is maintained by measuring the time dependent intensity using a split photodetector.

In another refinement of an embodiment of the invention the quadrature condition is maintained using an adaptive optic element.

Another embodiment according to the present invention includes a deflector unit composed of a lens that is translated laterally, thus deflecting the focused beam laterally on the target.

Another embodiment according to the present invention includes a deflector unit composed of an optical plate in the path of the beam that is tilted and thereby deflects the beam across the surface of the target.

Another embodiment according to the present invention includes an acoustic-optic modulator with a controllable frequency and telescopic lens to convert angular deflection by the modulator into linear deflection at the target surface.

Various embodiments disclosed herein are intended for use in scanning the small scale features of a surface of a stationary target including, but not limited to, biological substrates (such as chips or bioCDs) and electronic substrates (such as chips or semiconductor wafers). It should be understood that it is contemplated as within the scope of the invention that the target may be within a vacuum chamber and may be subject to interferometric detection (preferably quadrature interferometric detection) through, for example, a substantially transparent window into the chamber.

In one exemplary embodiment of the present invention, a programmed laser scanner scans over periodic or a-periodic patterns of immobilized biomolecules on a flat or curved surface.

Although the present invention has been described with reference to certain exemplary embodiments, it is understood that variations and modifications exist and are within the scope of the present invention.

BRIEF DESCRIPTION OF THE FIGURES

FIG. 10(a) shows a linear set of tracks. FIG. 10(b) shows the tracks can take on any 2D parametric transformation of generalized curvilinear coordinates $\xi(x,y)$, $\zeta(x,y)$. FIG. 10(c) shows the track trajectories can be general closed or open trajectories.

DETAILED DESCRIPTION

Figure 1:
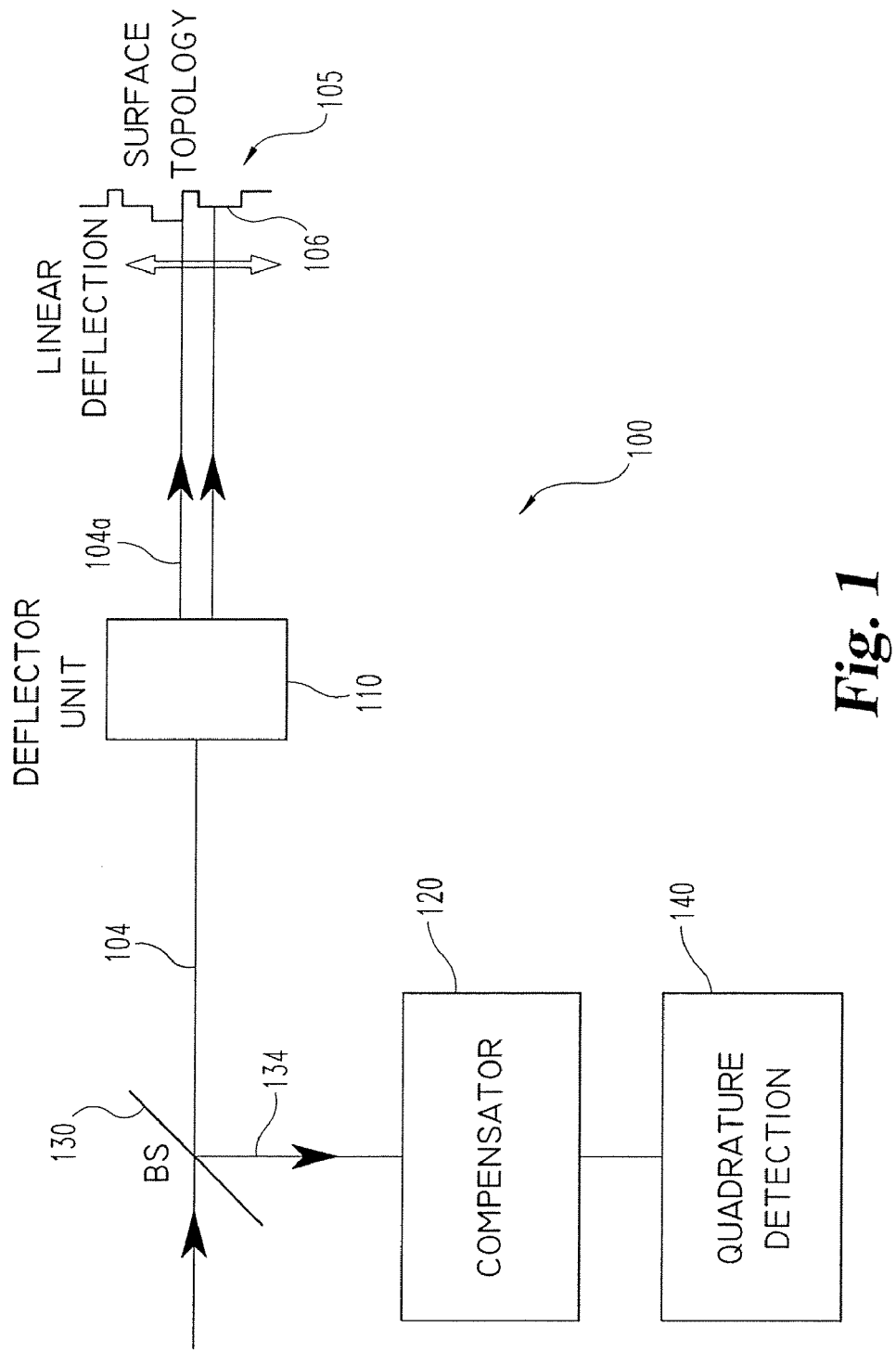
FIG. 1 illustrates one embodiment of a self-referencing laser scanning quadrature system.

The biological compact disc was introduced as a sensitive spinning-disk interferometer that operates at high-speed and is self-referencing [see M. M. Varma, H. D. Inerowicz, F. E. Regnier, and D. D. Nolte, "High-speed label-free detection by spinning-disk micro-interferometry," *Biosensors & Bioelectronics*, vol. 19, pp. 1371-1376, 2004]. Self-referencing is preferable in performing stable interferometry on a mechanically spinning disk. In order to be sensitive to optical path length, the relative phase between the signal and reference beams is locked to substantially quadrature ($\pi/2$ phase difference), preferably independent of mechanical vibrations or motion. Two quadrature interferometric detection classes of BioCD were previously defined. The micro-diffraction class ("MD-class") [see M. M. Varma, D. D. Nolte, H. D. Inerowicz, and F. E. Regnier, "Spinning-disk self-referencing interferometry of antigen-antibody recognition," *Optics Letters*, vol. 29, pp. 950-952, 2004. Also see U.S. Pat. No. 6,685,885 to Nolte et al] and the adaptive optic class ("AO-class") [see U.S. patent application Ser. No. 10/726,772 filed Dec. 3, 2003 entitled "Adaptive Interferometric Multi-Analyte High-Speed Biosensor", which is incorporated by reference herein in its entirety].

The MD-class BioCD locks to quadrature using microstructures fabricated on the disk that diffract a focused laser beam to the far field with a fixed relative phase. In one embodiment, gold spokes, preferably 1024 to a disk, that have a height of $\lambda/8$ are deposited by evaporation onto a reflecting surface, and bio-molecules are immobilized on either the gold spokes or the land. Because the phase difference is set by the height difference of the local microstructure, it is unaffected by mechanical motion or vibration. Immobilized bio-molecules change the relative phase which is converted to amplitude modulation in the far field.

The AO-class locks to quadrature using self-adaptive non-linear optical mixing, preferably in a photorefractive quantum well [see D. D. Nolte, "Semi-insulating semiconductor heterostructures: Optoelectronic properties and applications," *J. Appl. Phys.*, vol. 85, pp. 6259, 1999; D. D. Nolte and M. R. Melloch, "Photorefractive Quantum Wells and Thin Films," in *Photorefractive Effects and Materials*, D. D. Nolte, Ed. Dordrecht: Kluwer Academic Publishers, 1995] that adaptively tracks the phase between the signal and the reference [see D. D. Nolte, T. Cubel, L. J. Pyrak-Nolte, and M. R. Melloch, "Adaptive Beam Combining and Interferometry using Photorefractive Quantum Wells," *J. Opt. Soc. Am. B*, vol. 18, pp. 195-205, 2001]. In one embodiment, patterned protein structures modulate optical phase of the probe beam, which is sent to a photorefractive quantum well (PRQW) device and mixed with a reference local oscillator beam by two-wave mixing. The two-wave mixing self-compensates mechanical disturbances to maintain the quadrature condition with a compensation rate higher than a kHz. Phase modulation caused by protein structures on the spinning disk have frequencies higher than the compensation rate and is read out by photodetector. As previously noted, for further details of the AO-class see U.S. patent application Ser. No. 10/726,772 filed Dec. 3, 2003 entitled "Adaptive Interferometric Multi-Analyte High-Speed Biosensor", previously incorporated by reference herein in its entirety.

These BioCD quadrature classes traded off complexity between the near-field and the far-field. MID-class BioCDs appear to require more complex microstructuring on the disk, while AO-class disks required holographic films for the non-linear optical mixing. Thus, a third quadrature class analogous to phase-contrast imaging was developed that is referred to as the Phase-Contrast class ("PC-class"). The PC-class of quadrature interferometric detection is discussed in the previously mentioned U.S. Provisional Patent Application No. 60/649,070, filed Feb. 1, 2005, entitled "Phase-Contrast Quadrature For Spinning Disk Interferometry And Immunological Assay"; and U.S. Provisional Patent Application No. 60/755,177, filed Dec. 30, 2005, entitled "Phase-Contrast BioCD: High-Speed Immunoassays at Sub-Picogram Detection Levels". The PC-class of quadrature interferometric detection is further disclosed in U.S. patent application Ser. No. 11/345,462 being filed on the same day as the present application and entitled "Method and Apparatus for Phase Contrast Quadrature Interferometric Detection of an Immunoassay", previously incorporated herein by reference.

Prior to describing various embodiments of the present invention the intended meaning of quadrature in the quadrature interferometric detection systems of the present invention is further explained. In some specific applications quadrature might be narrowly construed as what occurs in an interferometric system when a common optical "mode" is split into at least 2 "scattered" modes that differ in phase about $N*\pi/2$ (N being an odd integer). However, as used in the present application an interferometric system is in quadrature when at least one mode "interacts" with a target region and at least one of the other modes does not, where these modes differ in phase by about $N*\pi/2$ (N being an odd integer). This definition of quadrature is also applicable to interferometric systems in which the "other mode(s)" interact with a different portion of the target. The interferometric system may be considered to be substantially in the quadrature condition if the phase difference is $\pi/2$ (or $N*\pi/2$, wherein N is an odd integer) plus or minus approximately twenty percent.

Additionally, prior to describing various embodiments of the present invention that make use of the previously mentioned (and previously incorporated herein by reference) PC-class disclosure relating to quadrature interferometric detection, the intended meaning of "edge" or "edge-detection" in the present application is set forth. Various portions of the description of one or more embodiments below might refer to an edge that diffracts light. It will be understood by those of ordinary skill in the art that the description for all embodiments disclosed herein of a step or an edge diffracting light in reality refers to the fact that light diffraction is integrated over the full optical wavefront. Strictly speaking it is not just the edge that diffracts light. It is the discontinuity or step that is integrated over the beam that diffracts to the far field and is detected. The discontinuity of the step of the differing heights places different conditions on the wave to the left and right. It is the integrated difference that is detected as diffraction, and not just a step or an edge. Moreover, with respect to the present application the term "edge" or "edge-detection" is intended to encompass generally the differential detection techniques disclosed herein. That is to say, quadrature interferometric detection that detects the slope or derivative of the surface height. The signal is proportional to dh(x)/dx. While more common usage of the term might indicate that only in the special case of a discontinuous step is something an "edge-detection" process, the terms as used herein are intended to be defined more broadly as set forth in this paragraph to also encompass "slope detection" across a step.

Interferometric detection in quadrature was generally considered to be incompatible with laser scanning. Most scanning systems operate on the principle of scattered light off diffuse targets, or absorption of light by opaque regions on targets. Among the difficulties with interferometry using laser scanning is the changing beam orientation and changing path lengths. These changing quantities make it difficult to lock the relative phase of a signal and a reference to π/2. The sensitivity advantage of interferometry, however, makes a compelling case to develop a stable means of locking to quadrature in a laser scanning system.

An important aspect of quadrature scanning is a stable phase relationship between a signal and a reference wave established through self-referencing. As discussed above, various patent applications describe the establishment of self-referencing interferometry through microdiffraction, adaptive optics and phase contrast on, for example, a spinning disk. In the spinning disk embodiments, a relevant feature is the capability of high speed optical sampling that shifts the measurement far from 1/f noise. The laser spot in these applications was preferably stationary. In the preferred embodiments of the present application, however, the target remains fixed while the laser is in motion. This simple difference (target fixed while laser in motion versus target in motion while laser fixed) creates non-trivial differences in the implementation of the optical system.

In one embodiment of the present invention, laser scanning with self-referencing quadrature preferably includes a displacement element to shift the beam laterally, a compensation element to compensate for the beam shift to keep optical path differences to much smaller than a wavelength, and quadrature detection that converts phase modulation into intensity modulation. This general system is shown in FIG. 1.

Operation of the system preferably includes high-speed dithering of the lateral beam displacement. Dithering means small excursions of the beam at high speed. The purpose of the dithering is to bring the frequency of the optical detection to high frequency far from 1/f noise. Those of ordinary skill in the art will understand that gross lateral displacements of the beam relative to the target could be accomplished either by shifting the target itself, or by the use of a larger but slower deflection superposed on top of the high-speed small dither. The small displacements in the high speed dither are preferably larger than the size of the laser focal spot. Focal spots can be quite small, down to microns, meaning that the dither displacement likewise may be only a few microns.

Referring to FIG. 1 there is shown a general self-referencing laser scanning quadrature system 100. System 100 comprises a deflector unit 110 that shifts and/or scans the incident probe beam 104 across the surface 106 of a target 105. System 100 further comprises a beam splitter 130 that redirects return signal beam 134 (resulting from beam 104a incident on surface 106 of target 105) toward a compensator 120 to keep optical path length changes to less that a wavelength. System 100 further includes quadrature detection 140 that converts phase modulation into intensity modulation.

Figure 2:
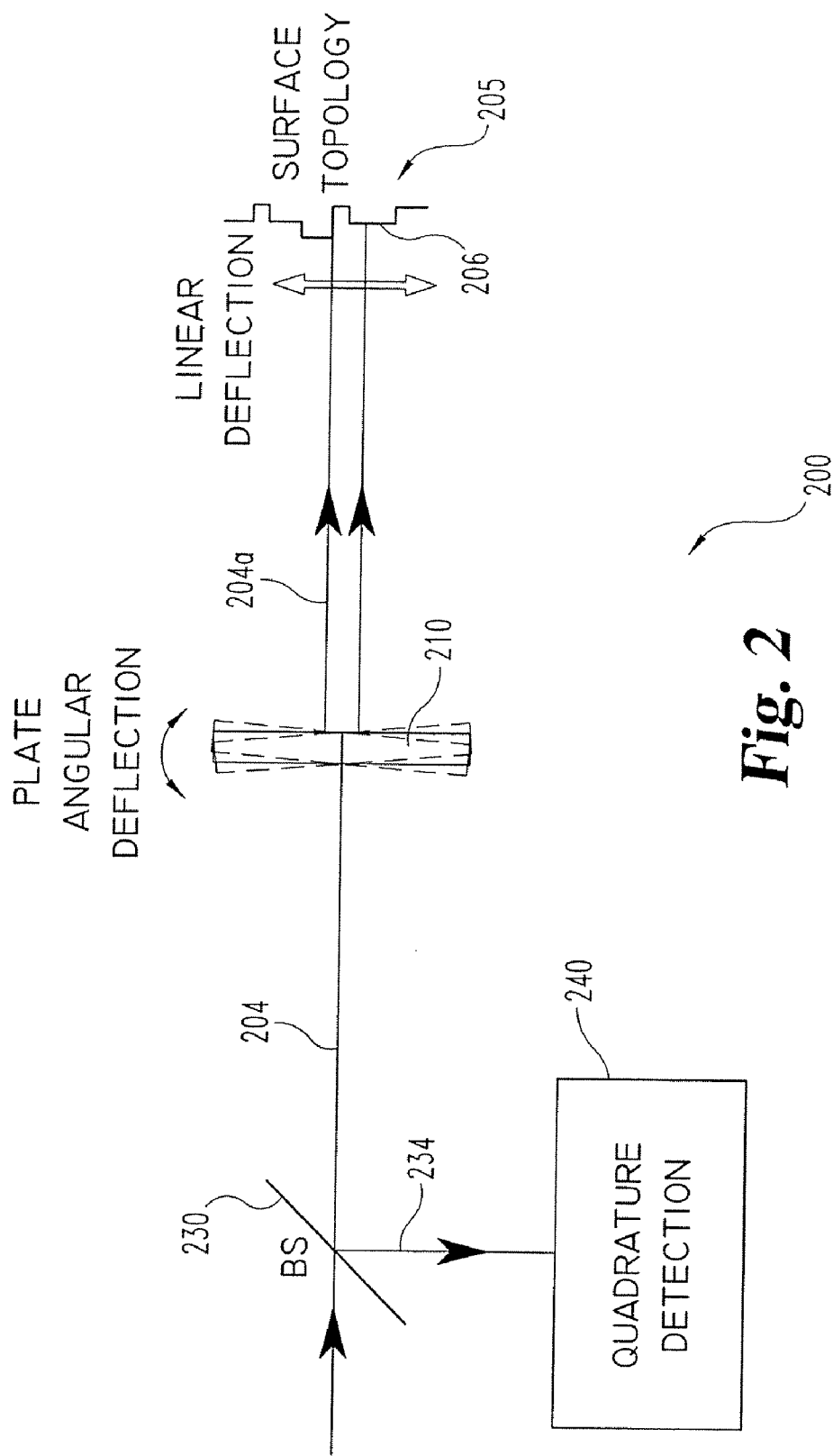
FIG. 2 illustrates an embodiment of a plane parallel plate self-referencing laser scanner.

With reference to FIG. 2 there is shown a plane parallel plate scanner 200. Incident probe beam 204 passes through plate 210. The plate 210 is preferably rotated at high speed to dither the laser spot of the incident probe beam 204a on the surface 206 of target 205. The return beams 234 retrace their paths exactly, providing for automatic compensation. System 200 further comprises a beam splitter 230 that redirects return signal beam 234 (resulting from beam 204a incident on surface 206 of target 205). System 200 further includes quadrature detection 240 that converts phase modulation from the target 205 into intensity modulation in the quadrature detection 240.

It should be understood that a wide variety of embodiments of means for scanning the laser beam across the surface of the target are contemplated as within the scope of the invention. That is to say, the deflector unit 110 can take a wide variety of forms that are disclosed herein. For example, as just discussed above and shown in FIG. 2, a plane-parallel optical plate 210 that is rotated in the incident beam 204 displaces the transmitted incident beam 204a parallel to the original beam direction. Similarly, the means for scanning can take the form of deflector mirror 310, acousto-optic crystal 410, or even lens 612 being deflected. Depending on the embodiment, the means for scanning might or might not include a lens in conjunction with some of the previously described structures. Some preferred embodiments of the means for scanning will permit beam dithering, but such is not necessary in all embodiments contemplated as within the scope of the invention.

With respect to the means for scanning of FIG. 2 (plane-parallel optical plate 210 that is rotated), the deflections are small, but consistent with beam dithering. As mentioned, an advantage of the plate scanner 200 is the automatic compensation of the beam motion by the beam returning through the plate 210. The rays will retrace their path to the beam-splitter 230, where the return signal beam 234 is directed to the quadrature detector 240. The high speed dither provides a well-defined detection frequency. Larger displacements of the beam to scan over the target may be accomplished by either translating the target, or by combining the plate dither with an additional displacement mechanism capable of large beam deflections, as described below.

Figure 3:
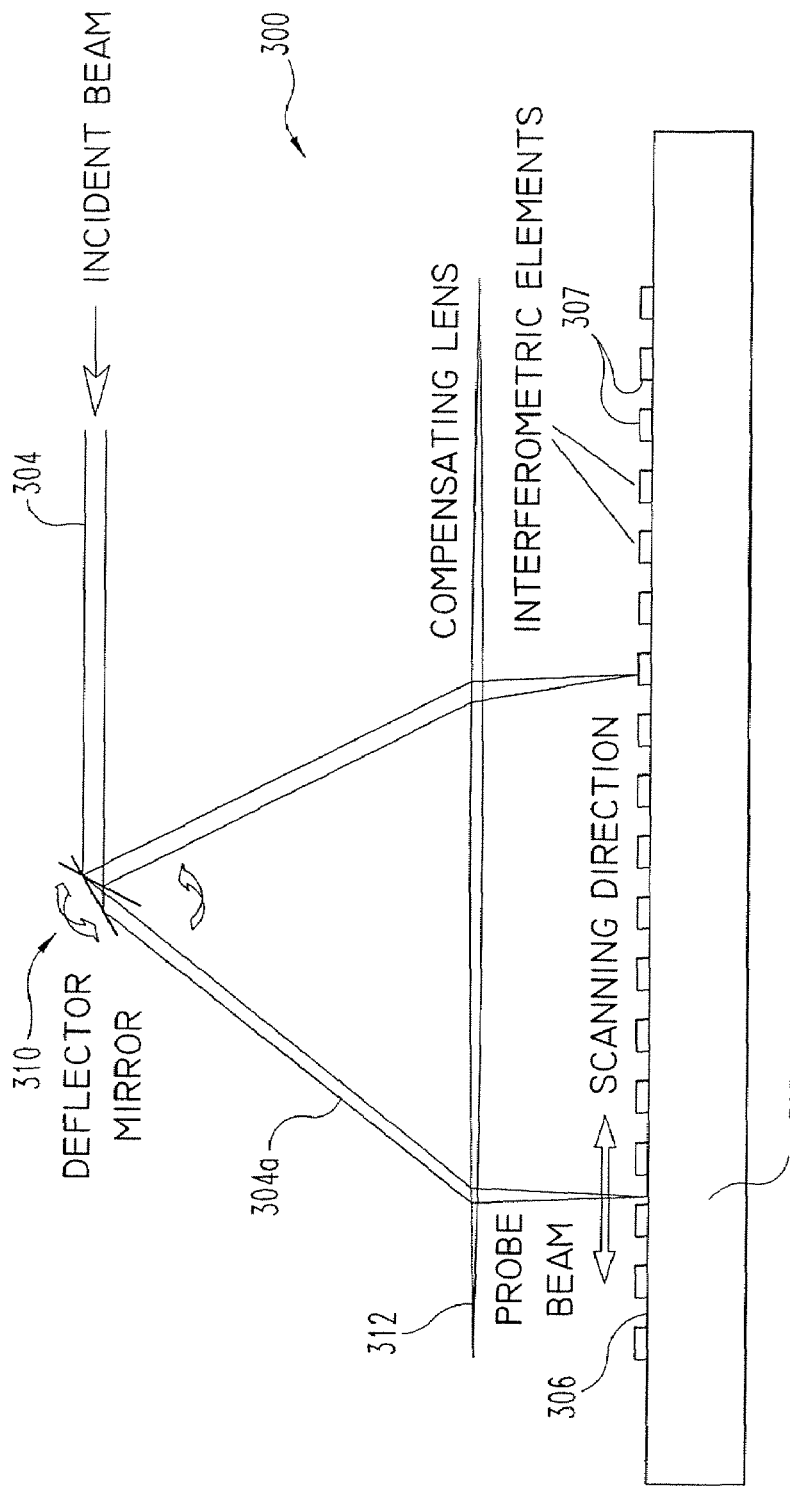
FIG. 3 illustrates an embodiment of a deflector mirror self-referencing laser scanner.

With reference to FIG. 3, there is shown a deflector mirror system 300 that redirects the incident beam 304 from the front focal point of a lens 312 into probe beam 304a toward surface 306 of target 305. Large displacements are possible in this configuration. High speed dither can be superposed on the slower larger displacements. That is to say, FIG. 3 shows an example wherein larger beam deflection is possible. This system 300 uses a conventional deflector mirror 310 as used in conventional laser scanner systems. The system 300 is telescopic, with the deflector 310 at the front focus of the compensator lens 312.

This system 300 has the advantage of larger displacements over the target substrate (examples of substrates including, but not limited to, chips such as biochips and electronic chips). On top of the large displacement, high-speed small-scale dither can be superposed in the drive circuit (not shown) of the deflector mirror 312. The deflector mirror 312 might, for example, be mounted on galvonometer drives, but can also be the facets of a rhomb that is spinning on a motor. The advantage of the rhomb is the high speed attainable with rotating systems that can rotate up to 6000 rpm. The large beam displacements in these systems can cover large areas of stationary chips in a short time. FIG. 3 depicts a linear laser scanning arrangement with interferometric elements arrayed along linear tracks on a planar substrate. The deflecting mirror scans the laser spot along the tracks. It should also be understood that while system 300 is shown as having a target 305 with a plurality of interferometric elements 307, the system 300 is more generally applicable for use in surface metrology that does not include interferometric elements 307, and that is not laid out along linear tracks. For example, generalized two dimensional scanning is contemplated as within the scope of the invention as is illustrated in FIGS. 10(a)-(c) and described below. It should also be understood that a wide variety of scanning configurations, linear or otherwise, are contemplated as within the scope of the invention.

Figure 4:
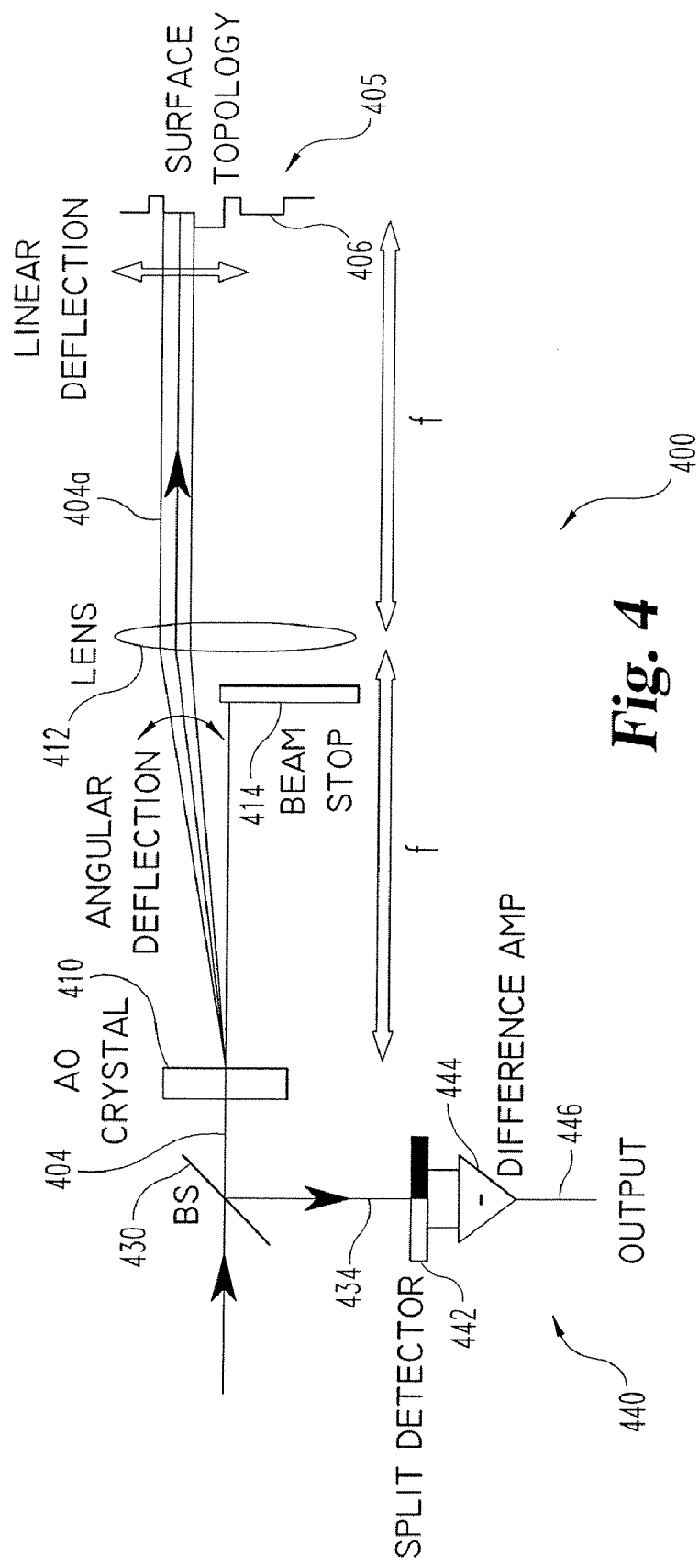
FIG. 4 illustrates an embodiment of an acousto-optic self-referencing laser scanner shown in phase-contrast quadrature.

In another embodiment of the invention, the deflector unit 110 can be an acousto-optic modulator, as shown in FIG. 4. The acousto-optic crystal 410 supports a high-frequency sound wave that diffracts incident light 404 at an angle. The angle of diffraction is a function of the sound frequency, that can be adjusted. By sweeping the sound frequency in the crystal, the angular deflection is swept. The AO crystal 410 is preferably at the front focal point of the lens 412, and the beam 404a is focused onto the surface 406 of target 405. The system 400 preferably includes a beam stop 414 to block a portion of the incident beam 404 that might otherwise pass through the center of the lens. The return beam retraces the path to the AO modulator where it is diffracted back toward the source. The beam splitter 430 redirects the return light 434 for quadrature detection 440. In FIG. 4, quadrature detection 440 is in the form of a split detector 442 operating in phase-contrast quadrature that is preferably used in conjunction with differential amplifier 444 to produce output 446. In this system the dither is accomplished by superposing a high-speed frequency modulation on top of a slower scan frequency sweep.

The acousto-optic scanning system 400 shown in FIG. 4 preferably makes use of phase-contrast quadrature detection 440 [see U.S. patent application Ser. No. 11/345,462 being filed on the same day as the present application and entitled "Method and Apparatus for Phase Contrast Quadrature Interferometric Detection of an Immunoassay", previously incorporated herein by reference]. There are preferably no moving parts giving this system 400 the capability of extremely high scan speeds and detection frequencies. That is to say, the absence of any moving parts makes this scanning capable of extremely high speeds in the MHz range, which is the frequency ranges where laser sources have lowest noise and can approach the shot-noise limit.

Figure 5:
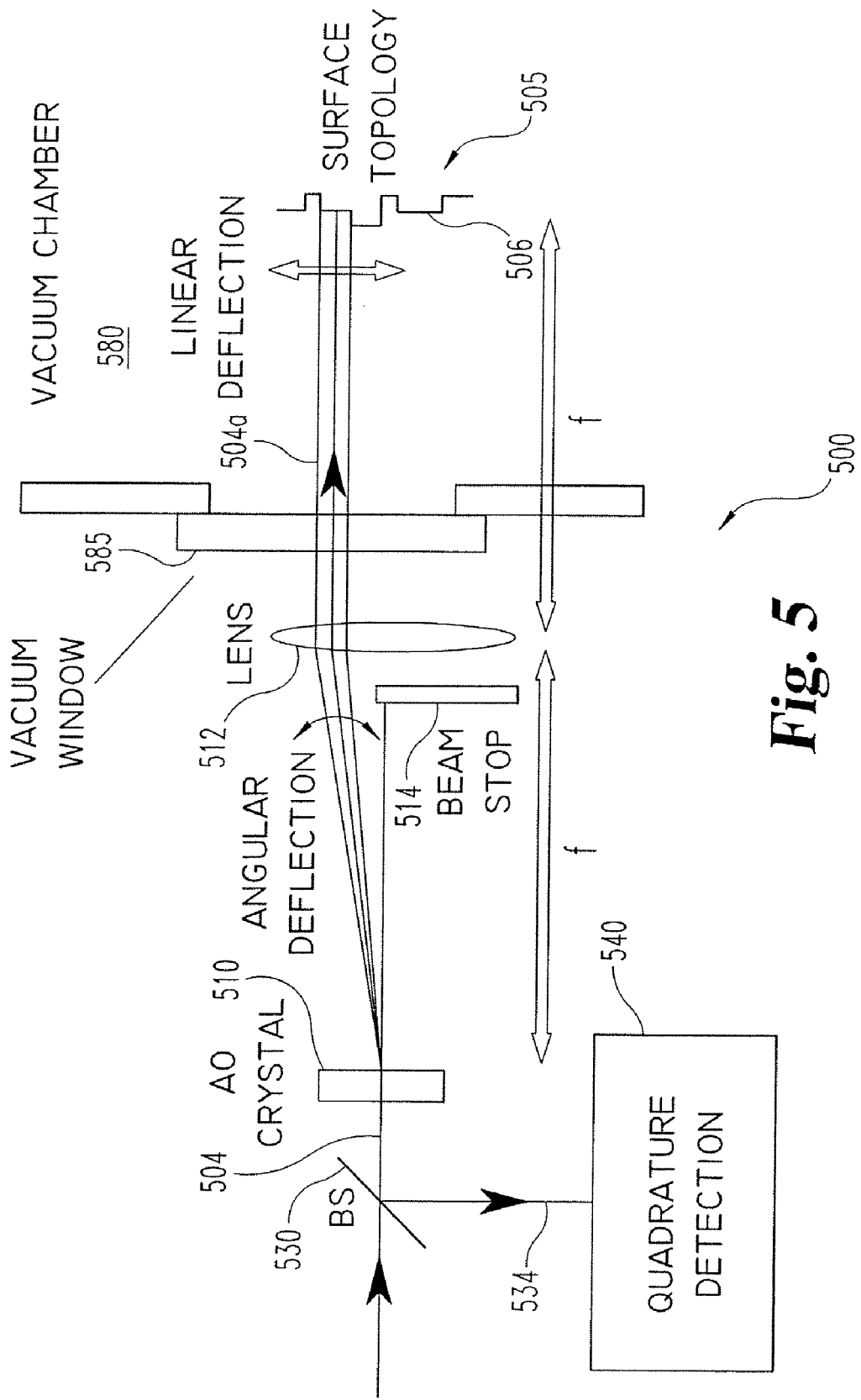
FIG. 5 illustrates an example of an application of a laser scanning quadrature system in which the target is inside a vacuum system.

An example of one application of the scanning quadrature system will now be briefly discussed. With reference to FIG. 5 there is shown a scanner 500 that makes use of a probe beam that is transmitted through the high-vacuum window 585 of a vacuum chamber 580 to probe a surface 506 of a target 505 inside the chamber 580. The target 505 can be in a bioreactor, or in a materials processing system, such as a metal evaporator or a plasma etch system. Metal evaporation and plasma etching are extremely critical parts of semiconductor processing, and thickness monitoring of this process is critical. For instance, in Intel chips the thickness of the gate oxide must be monitored to nanometer accuracies during plasma etch.

The embodiment of FIG. 5 would be capable of this metrology application. With reference to FIG. 5, there is shown an example of an application in which the target 505 is inside a vacuum chamber 580. Optical access to the target is through the preferably substantially transparent vacuum window 585. This is an example of the utility of the scanning quadrature system in which the target either cannot move or is substantially stationary, yet all the advantages of high-speed quadrature detection can still be achieved.

With reference to FIG. 5, the generic deflector unit 110 is again preferably an acousto-optic modulator. The acousto-optic crystal 510 supports a high-frequency sound wave that diffracts incident probe light 504 at an angle. The angle of diffraction is a function of the sound frequency, that can be adjusted. By sweeping the sound frequency in the crystal, the angular deflection is swept. The AO crystal 510 is preferably at the front focal point of the lens 512, and the beam 504a is focused onto the surface 506 of target 505 through vacuum window 585. The system 500 preferably includes a beam stop 514 to block a portion of the incident beam 504 that might otherwise pass through the center of the lens. The return beam 534 retraces the path to the AO modulator where it is diffracted back toward the source. The beam splitter 530 redirects the return light 534 to quadrature detection 540. As in FIG. 4, quadrature detection 540 is preferably a split detector operating in phase-contrast quadrature.

Figure 6:
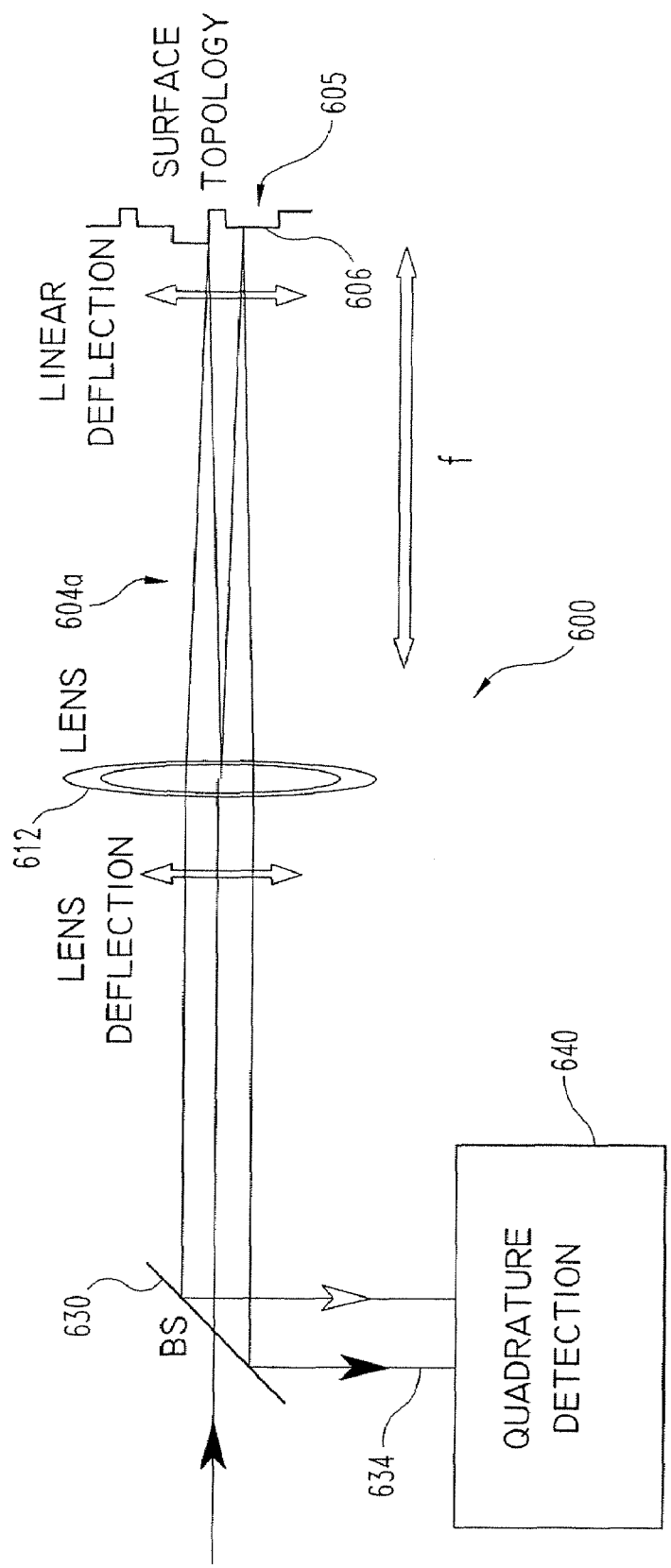
FIG. 6 illustrates an embodiment of a simple lens deflection system without compensation.

It should be understood that a wide variety of laser scanning interferometric surface metrology systems are contemplated as within the scope of the invention. For example, not all embodiments of the scanning system require all elements of FIG. 1. Referring to FIG. 6, there is shown a scanner 600. Scanner 600 is a more simple implementation that uses a lens 612 on a galvonometer mount. This type of lens system is used routinely in the read head of compact disc players. When the lens 612 is deflected, the focused beam 604a is deflected. The return beam 634 in this case does not exactly retrace the incident beam 604, thus causing beam "walk-off" on the quadrature detector 640. Nonetheless, by the use of only small-amplitude dither, this walk-off effect can be small enough to allow linear scanning and quadrature detection.

Figure 7:
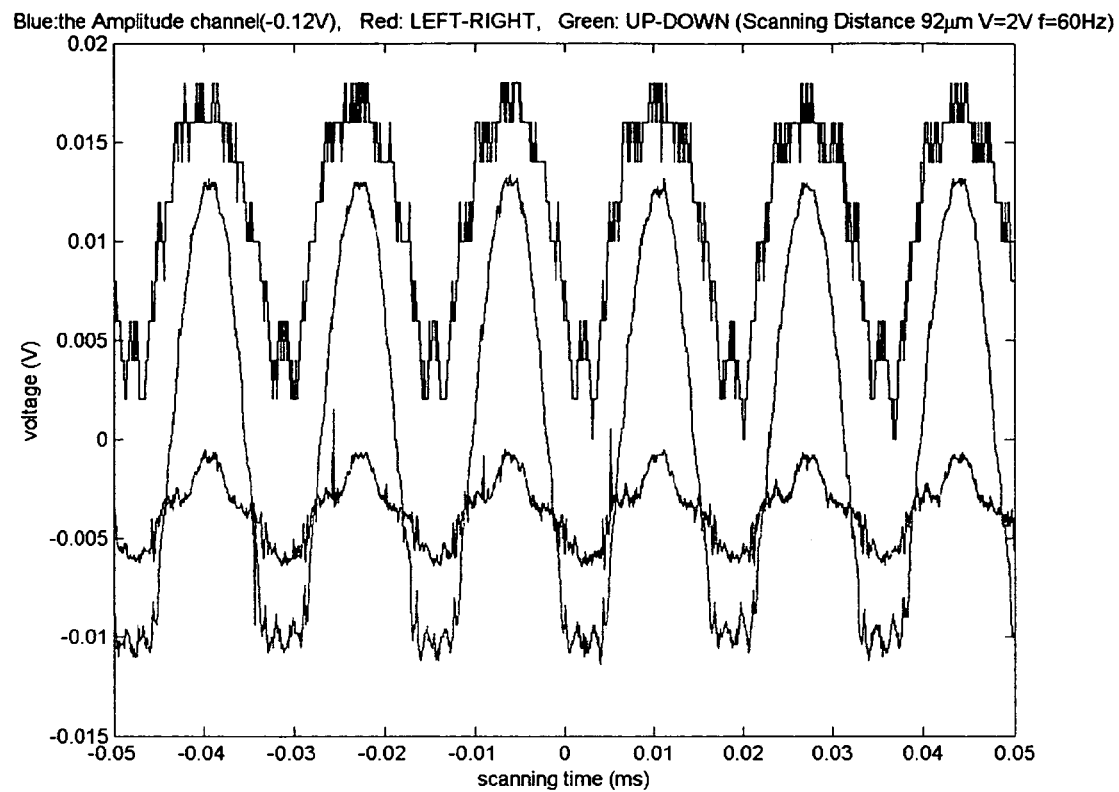
FIG. 7 illustrates time trace of amplitude channel and both phase channels.

A time trace of the system of FIG. 6 is shown in FIG. 7, with a phase-contrast detection showing the amplitude channel and the two orthogonal phase channels. The amplitude channel is the upper trace. The left-right channel is the middle trace. The up-down channel is the lower trace. The walk-off effect causes the largest part of the signal modulation. However, by demodulating the slow walk-off effect, the high-frequency part contains the quadrature information. That is to say, the modulation is dominated by the walk-off, but the smaller structures show positive detection of a monolayer of antibody protein on a silicon wafer.

Figure 8:
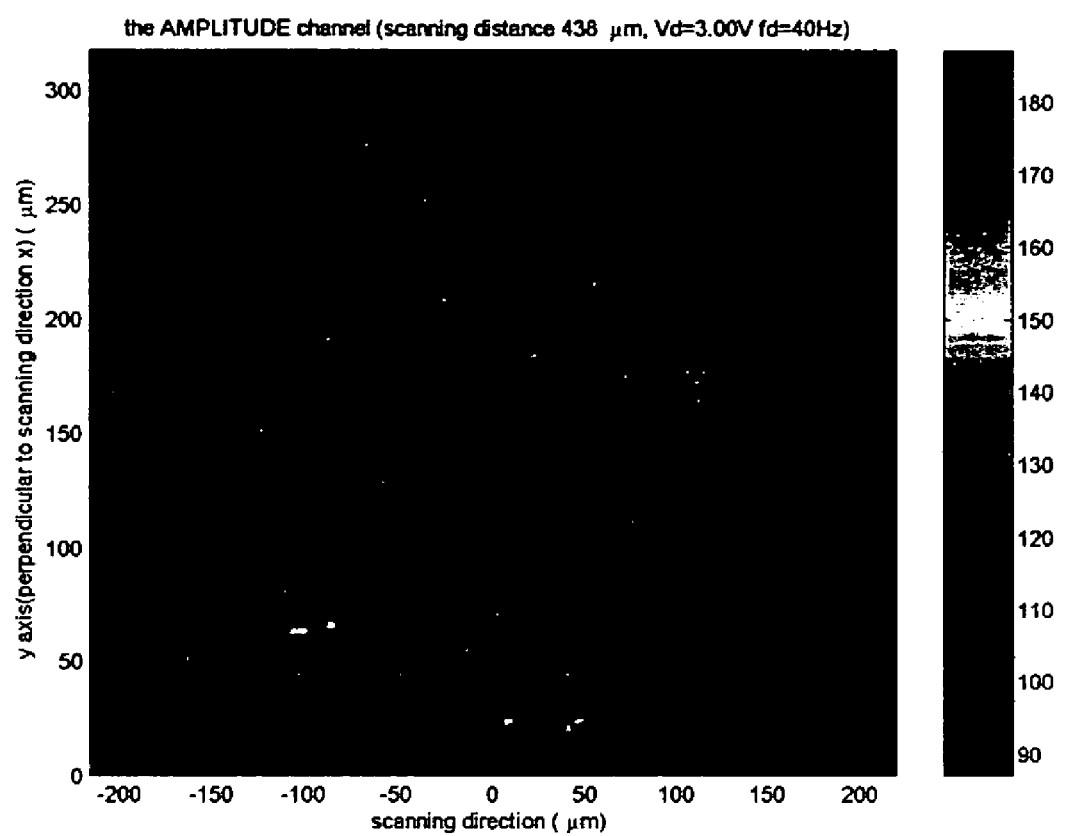
FIG. 8 illustrates the amplitude channel after demodulating beam walk-off showing a monolayer of printed antibody protein on a silicon wafer.
Figure 9:
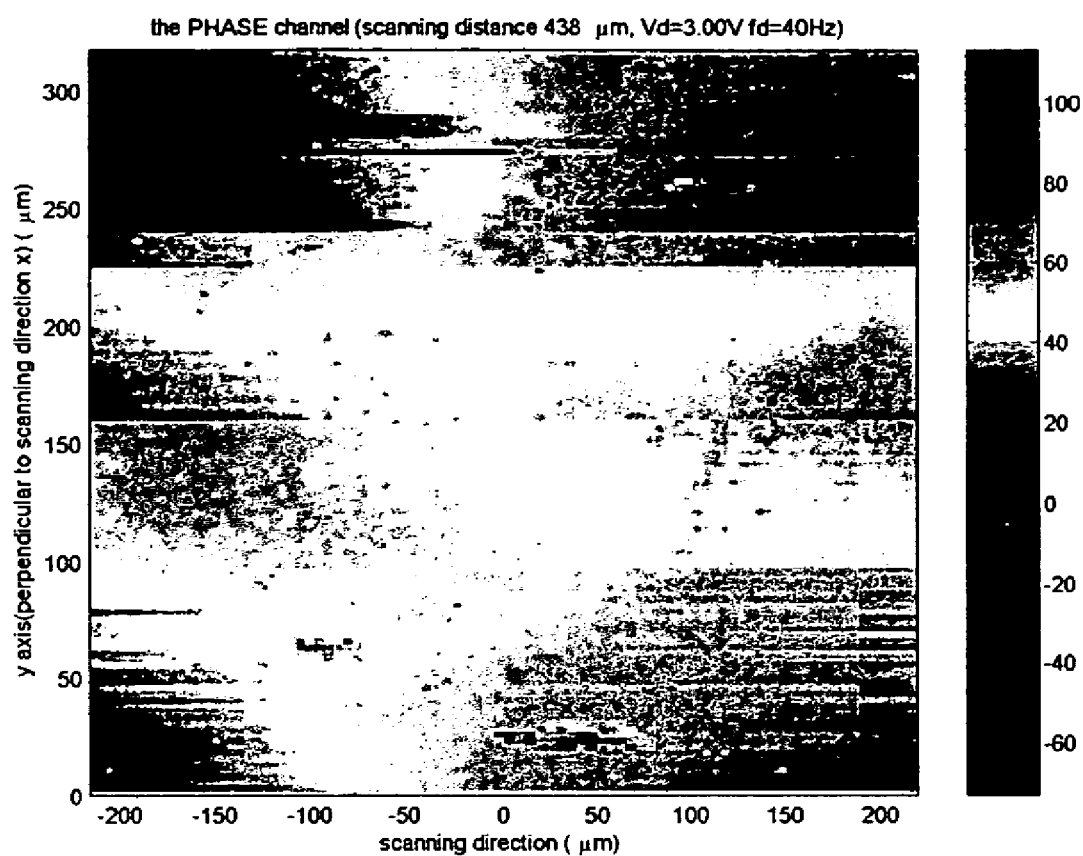
FIG. 9 illustrates the phase channel showing protein edge in the edge-detection mode of phase-contrast quadrature.

The use of this system to image protein printed on the surface of $SiO_2$/Si is shown in FIG. 8 and FIG. 9 for the amplitude and phase channels, respectively. With reference to FIG. 8 there is shown the amplitude channel after demodulating beam walk-off showing a monolayer of printed antibody protein on a silicon wafer. With reference to FIG. 9 there is shown the phase channel showing protein edge in the edge-detection mode of phase-contrast quadrature.

Figure 10:
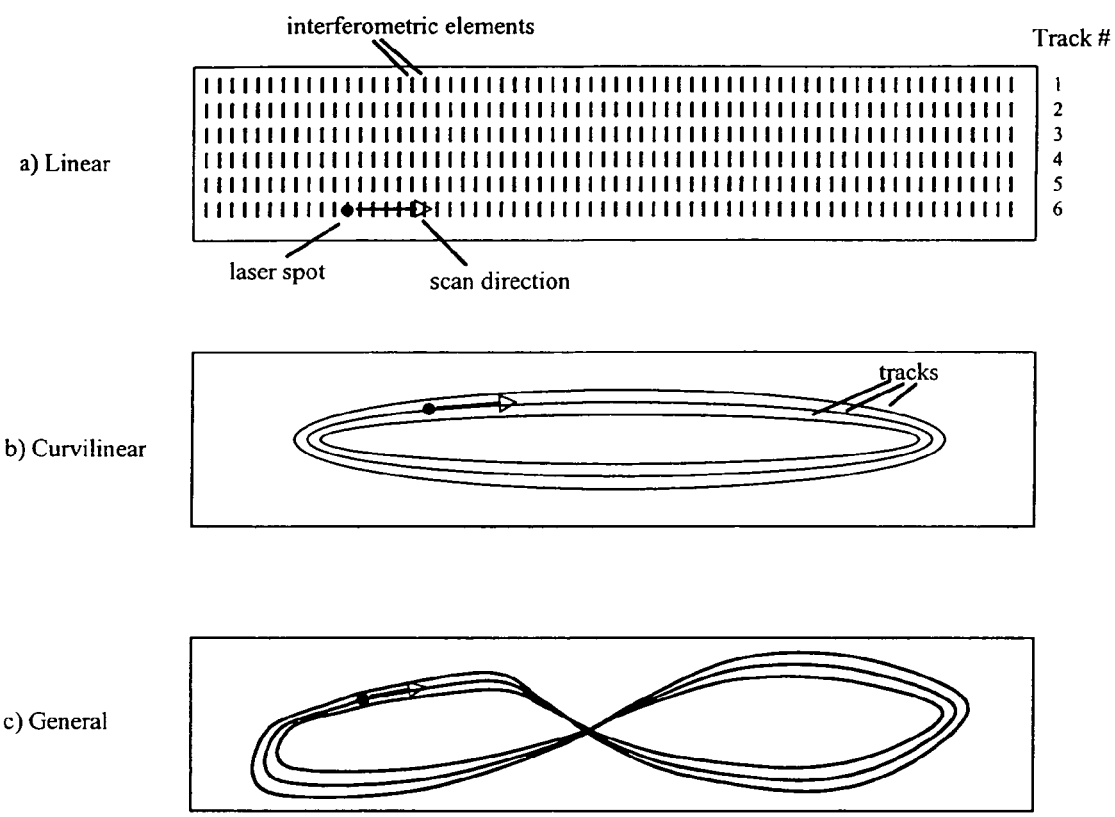
FIGS. 10(a)-(c) illustrates various embodiments of laser scanning track trajectories in two dimensions.

FIG. 10 illustrates possible scanning coordinates in two dimensions. It is understood that it is contemplated as within the scope of the invention that scanning can be accomplished in a wide variety of two-dimensional coordinate systems. Examples of this are illustrated in FIG. 10 where the trajectories are parametric trajectories in generalized curvilinear coordinates ξ(x,y), ζ(x,y). The trajectory is parameterized in time as ξ(t), ζ(t). The trajectories can be generalized arcs or segments that are open or closed, non-crossing or crossing.

In one exemplary embodiment of the present invention, a laser source, one or more steering mirrors, compensating optics, and interferometric elements arrayed along successive tracks in a two-dimensional plane are provided. The steering mirrors can move the probe laser spot in any number of trajectories across the biochip surface. As previously noted, a linear scanning arrangement is shown in FIG. 3. A linear scanning arrangement is also shown in FIG. 10a. In FIG. 10b, the trajectories are parametric trajectories in generalized curvilinear coordinates ξ(x,y), ζ(x,y). The trajectory is parameterized in time as ξ(t), ζ(t). In FIG. 10c, the trajectories are generalized arcs or segments that are open or closed, non-crossing or crossing. Thus, various applications of the present invention permit measurement of the molecular or cellular or particulate content of a liquid or gas sample in which an analyte binds to a substrate along lines, arcs or curves that are not localized in at least one spatial dimension of a generalized coordinate frame.

It should be understood that a wide variety of detector configurations are contemplated as within the scope of the invention for use as means for detecting a return signal in a substantially quadrature condition in, for example, embodiments of the present invention such the illustrated systems 100, 200, 300, 400, 500 and 600. For example, for MD-class systems the quadrature detection described in FIGS. 1-10 of U.S. application Ser. No. 10/726,772 filed Dec. 3, 2003 entitled "Adaptive Interferometric Multi-Analyte High-Speed Biosensor" (published as US 2004/0166593 on Aug. 26, 2004) might be used. This application was previously incorporated herein by reference. Similarly, the quadrature detection in the AO-class of detection disclosed in the remaining portion of U.S. application Ser. No. 10/726,772 (in particular see FIGS. 17-21) might be used. For example, such quadrature detection might make use of two photodetectors in conjunction with an adaptive element such as a photorefractive quantum well, photorefractive polymer, or general photorefractive material which exhibits the photorefractive effect. Furthermore, the means for detecting the return signal in a substantially quadrature condition might also be the structures disclosed for detection in U.S. patent application Ser. No. 11/345,462 being filed on the same day as the present application and entitled "Method and Apparatus for Phase Contrast Quadrature Interferometric Detection of an Immunoassay", previously incorporated herein by reference. Those structures included various split photodetector configurations including, but not limited to, split-ring photodetector, quadrant photodetector, separate photodetectors or detector arrays (positioned in such a manner so as to detect the return signal in substantially one or both quadrature conditions). Such structures preferably were supplemented with an inversion circuit and summation circuit for inversion of the output of one substantially quadrature condition and summation of the inverted first output with the output for the second substantially quadrature condition.

It should also be understood that improvements in, for example, signal to noise ratio and other aspects of the invention(s) disclosed in U.S. patent application Ser. No. 11/345,566 being filed on the same day as the present application that claims priority to this provisional application and entitled "Differentially Encoded Biological Analyzer Planar Array Apparatus and Methods" (previously incorporated herein by reference) are contemplated for use with and as within the scope of the present invention.

While the present system is susceptible to various modifications and alternative forms, exemplary embodiments thereof have been shown by way of example in the drawings and will herein be described in detail. It should be understood, however, that there is no intent to limit the system to the particular forms disclosed, but on the contrary, the intention is to address all modifications, equivalents, and alternatives falling within the spirit and scope of the system as defined by the appended claims.

What is claimed is:

1. An apparatus for assessing topology of a surface of a target, comprising:

an optical source for generating a single incident laser beam;

means for scanning the single incident laser beam across at least a portion of the surface of the target, wherein the surface of the target is adapted to reflect the single incident laser beam therefrom as a single self-referencing return beam, the single self-referencing return beam containing signal and reference components; and a beamsplitter positioned to redirect the single self-referencing return beam toward a means for detecting the single self-referencing return beam in a substantially quadrature condition.

2. The apparatus of claim 1, wherein the means for scanning includes a parallel plate.

3. The apparatus of claim 2, wherein the means for scanning further includes a galvanometer for rotating the parallel plate at high speed.

4. The apparatus of claim 1, wherein the means for scanning includes a deflector mirror.

5. The apparatus of claim 4, wherein the means for scanning further includes a galvanometer for rotating the deflector mirror at high speed.

6. The apparatus of claim 1, wherein the means for scanning is a lens that is laterally deflected.

7. The apparatus of claim 1, wherein the means for scanning includes an acousto-optic modulator.

8. The apparatus of claim 7, further including a lens with a focal length f for focusing the incident laser beam with a waist $w_0$ on the surface of the target, the lens being positioned between the means for scanning and the target.

9. The apparatus of claim 8, wherein the means for detecting the return beam in a substantially quadrature condition includes an adaptive optic element used in conjunction with two separate photodetectors.

10. The apparatus of claim 9, wherein the adaptive optic element is a photorefractive quantum well.

11. The apparatus of claim 8, wherein the means for detecting the return beam in a substantially quadrature condition includes a split photodetector.

12. The apparatus of claim 11, wherein the incident laser beam has a wavelength λ, and wherein the split photodetector is a detector away positioned at a pair of quadrature angles $\theta_q$, the quadrature angles being defined from a ray normal to the target by a formula: $\theta_q = \sin^{-1}(\lambda/2w_o)$.

13. The apparatus of claim 11, further including an inverting circuit connected to the split photodetector and a summing circuit connected to both the split photodetector and to the inverting circuit.

14. The apparatus of claim 8, wherein the acousto-optic modulator is offset from the lens by a distance f, and wherein the lens is offset from the surface of the target by a distance f.

15. A quadrature interferometric method for determining the presence or absence of a target analyte in a sample, comprising:

generating a single incident beam having a wavelength $\lambda$ and a waist $w_o$ to probe at least a portion of a substrate having a reflecting surface that has been exposed to the sample, the reflecting surface including at least a first region having a layer of recognition molecules specific to the target analyte and a second region that does not include a layer of recognition molecules specific to the target analyte;

scanning the first region and the second region with the single incident beam while the substrate is maintained in a substantially fixed position, the single incident beam being reflected to generate a single self-referencing diffracted beam that includes signal and reference components; and measuring a time dependent intensity of the single self-referencing diffracted beam.

16. The method of claim 15, wherein the scanning is done using an acousto-optic modulator in conjunction with a lens.

17. The method of claim 16, wherein the diffracted beam is measured using a split-photodetector configuration, further comprising inverting a first output portion of the diffracted beam corresponding to one of a pair of quadrature angles, and summing the inverted first output with a second output of the diffracted beam corresponding to the other of the pair of quadrature angles.

18. The method of claim 17, wherein the reflecting surface is substantially flat and the quadrature angles are defined from a ray normal to the substrate by a formula: $\theta_q = \sin^{-1}(\lambda/2w_o)$.

19. The method of claim 17, wherein the reflecting surface of the substrate includes a plurality of lands and a plurality of ridges, the ridges having a height h, and the quadrature angles are defined from a ray normal to the substrate by a formula: $\theta_q = \sin^{-1}[(\lambda/2 - 4h)/w_o]$.

20. The method of claim 16, wherein scanning is sweeping an angular deflection by sweeping a sound frequency in the acousto-optic modulator, and further comprising dithering the probe laser beam, wherein the dithering is accomplished by superposing a high speed frequency on top of the slower scan frequency sweep.

21. The method of claim 15, further comprising dithering the incident beam.

22. A method for a high rate of inspection of a surface of a target using laser scanning quadrature interferometric detection, comprising:

generating a single probe laser beam having a wavelength $\lambda$;

passing the single probe laser beam through an acousto-optic modulator for angular deflection of the probe laser beam and then passing the deflected beam through a lens having a focal length f to focus the probe laser beam to a single incident beam having a waist $w_o$ on the surface of the target, wherein the surface of the target is adapted to reflect the single incident beam therefrom as a single self-referencing diffracted beam, the single self-referencing diffracted beam including signal and reference components; and measuring a time dependent intensity in a substantially quadrature condition of the reflected single self-referencing diffracted beam, the scanning occurring via controlling the angular deflection caused by the acousto-optic modulator.

23. The method of claim 22, further comprising dithering the probe laser beam.

24. The method of claim 22 wherein the quadrature condition is maintained by measuring the time dependent intensity using a split photodetector.

25. The method of claim 22, wherein the quadrature condition is maintained using an adaptive optic element.

26. An apparatus for assessing topology of a surface of a target, comprising:

an optical source for generating a probe laser beam;

means for scanning the probe laser beam across at least a portion of the surface of the target, the means for scanning including an acousto-optic modulator;

a lens with a focal length f for focusing the probe laser beam with a waist $w_0$ on the surface of the target, the lens being positioned between the means for scanning and the target; and a beamsplitter positioned to redirect a self-referencing return signal toward a means for detecting the return signal in a substantially quadrature condition, the return signal resulting from reflection of the probe laser beam off the surface of the target, wherein the means for detecting the return signal includes an adaptive optic element used in conjunction with two separate photodetectors.

27. The apparatus of claim 26, wherein the adaptive optic element is a photorefractive quantum well.

28. A method for a high rate of inspection of a surface of a target using laser scanning quadrature interferometric detection, comprising:

generating a probe laser beam having a wavelength $\lambda$;

passing the probe beam through an acousto-optic modulator for angular deflection of the probe beam and then passing the deflected beam through a lens having a focal length f to focus the probe beam to a waist $w_o$ on the surface of the target; and measuring a time dependent intensity in a substantially quadrature condition of a reflected diffraction signal resulting from scanning the probe beam across at least a portion of the surface of the target, the scanning occurring via controlling the angular deflection caused by the acousto-optic modulator, wherein the quadrature condition is maintained using an adaptive optic element.

* * * * *

UNITED STATES PATENT AND TRADEMARK OFFICE
CERTIFICATE OF CORRECTION

PATENT NO. : 7,405,831 B2 Page 1 of 1
APPLICATION NO. : 11/345564
DATED : July 29, 2008
INVENTOR(S) : Nolte et al.

It is certified that error appears in the above-identified patent and that said Letters Patent is hereby corrected as shown below:

Column 12, line 55, replace the term "away" with the term --array--

Signed and Sealed this

Twenty-third Day of September, 2008

JON W. DUDAS
*Director of the United States Patent and Trademark Office*